US012746484B2

(12) United States Patent
Park et al.

(10) Patent No.: US 12,746,484 B2
(45) Date of Patent: Sep. 29, 2026

(54) METHOD FOR REMOVING HCL IN CHLORINATION REACTION

(71) Applicant: HANWHA SOLUTIONS CORPORATION, Seoul (KR)

(72) Inventors: Jinho Park, Daejeon (KR); Namjin Jang, Daejeon (KR); Ji Hye Choi, Daejeon (KR)

(73) Assignee: HANWHA SOLUTIONS CORPORATION, Seoul (KR)

( * ) Notice: Subject to any disclaimer, the term of this patent is extended or adjusted under 35 U.S.C. 154(b) by 246 days.

(21) Appl. No.: 18/256,940

(22) PCT Filed: Dec. 14, 2021

(86) PCT No.: PCT/KR2021/018945
§ 371 (c)(1),
(2) Date: Jun. 12, 2023

(87) PCT Pub. No.: WO2022/131737
PCT Pub. Date: Jun. 23, 2022

(65) Prior Publication Data

US 2024/0033654 A1 Feb. 1, 2024

(30) Foreign Application Priority Data

Dec. 14, 2020 (KR) ........................ 10-2020-0174057

(51) Int. Cl.
*C07C 17/12* (2006.01)
*B01D 3/38* (2006.01)

(52) U.S. Cl.
CPC ................ *B01D 3/38* (2013.01); *C07C 17/12* (2013.01); *B01D 2257/204* (2013.01); *B01D 2257/2045* (2013.01)

(58) Field of Classification Search
CPC .... C07C 17/12–14; C07C 17/383–386; B01D 3/38
See application file for complete search history.

(56) References Cited

U.S. PATENT DOCUMENTS 6,265,628 B1 * 7/2001 Commandeur ......... C07C 17/14 204/157.99
2014/0018595 A1 1/2014 Spuhl
2016/0347625 A1 * 12/2016 Dalary ..................... B01D 3/38

FOREIGN PATENT DOCUMENTS

| | | | |
|---|---|---|---|
| EP | 0 870 748 | A1 | 10/1998 |
| EP | 1 760 060 | A1 | 3/2007 |
| GB | 833 850 | A | 5/1960 |
| KR | 10-2007-0067117 | A | 6/2007 |
| KR | 10-1332914 | B1 | 11/2013 |
| KR | 10-1773588 | B1 | 8/2017 |
| KR | 10-2017-0121159 | A | 11/2017 |
| WO | 2010/110163 | A1 | 9/2010 |
| WO | 2015/014784 | A1 | 2/2015 |
| WO | 2016/060834 | A1 | 4/2016 |

OTHER PUBLICATIONS

English machine translation of WO 2010/110163 (Year: 2010).*
An office action issued on Sep. 14, 2023, for corresponding KR Patent Application.
European Search Report issued on Mar. 21, 2025.
International Search Report Dated Mar. 29, 2022.
CN Office Action dated Jun. 26, 2025.

* cited by examiner

*Primary Examiner* — Renee Robinson
(74) *Attorney, Agent, or Firm* — Harvest IP Law, LLP

(57) ABSTRACT

The present invention relates to a method for removing HCl in a chlorination reaction, and more particularly, to a method capable of efficiently removing HCl produced during a chlorination reaction of an aromatic compound. The present invention includes, in a chlorination reaction in which a final product with a chlorine-substituted terminal is produced in column reactors connected to each other in series, heating hydrogen chloride produced in the chlorination reaction in a stripping column connected to the reactor positioned at the rearmost end, to remove hydrogen chloride.

8 Claims, No Drawings

METHOD FOR REMOVING HCL IN CHLORINATION REACTION

TECHNICAL FIELD

The present invention relates to a method for removing HCl in a chlorination reaction, and more particularly, to a method capable of efficiently removing HCl produced during a chlorination reaction of an aromatic compound.

BACKGROUND ART

Chlorobenzene or chlorotoluene is a material used in various industrial fields and is formed by a chlorination reaction of aromatic compounds such as benzene and toluene.

As a specific example, monochlorotoluenes such as o-chlorotoluene and p-chlorotoluene may be produced by reacting toluene with chlorine in the presence of a catalyst such as $FeCl_3$. Specifically, when toluene is allowed to react with chlorine in the presence of a catalyst, the chlorine atoms are substituted to produce monochlorotoluenes such as o-chlorotoluene and p-chlorotoluene.

During a chlorination reaction of such an aromatic compound, hydrogen chloride (HCl) is produced as a by-product.

In the related art, in order to remove by-products including a catalyst and hydrogen chloride contained in a reactant, a large amount of basic aqueous solution such as a sodium hydroxide aqueous solution has been added to the reactant, but there is a problem in that a large amount of wastewater is finally generated in an amount that is as much as the basic aqueous solution used. In addition, when the basic aqueous solution is used, unreacted toluene and moisture come into contact with each other to form an azeotrope, and therefore, a considerable amount of moisture is included in the recovered toluene. Accordingly, in order to reuse the recovered toluene in the reaction, azeotropic distillation for removing moisture is required, and azeotropic distillation is a process that consumes a large amount of energy, which causes an increase in manufacturing cost.

Accordingly, in Korean Patent No. 10-1773588 filed by the present applicant, unreacted toluene is first distilled for separation and recovery from a reaction product, and then the remaining product is brought into contact with a sodium hydroxide aqueous solution to remove a catalyst, such that the contact between the unreacted toluene and the sodium hydroxide aqueous solution is fundamentally blocked, thereby minimizing the content of moisture in recovered unreacted toluene.

However, there is still a problem in that a large amount of wastewater is generated since a basic aqueous solution such as a sodium hydroxide aqueous solution is used to remove the catalyst and the by-products such as HCl from the reaction product.

Therefore, the present inventors have conducted intensive studies on an efficient HCl removal method capable of significantly reducing the amount of wastewater discharged by removing hydrogen chloride gas without using a basic aqueous solution such as a sodium hydroxide aqueous solution.

DISCLOSURE

Technical Problem

An object of the present invention is to provide a method capable of efficiently removing HCl produced during a chlorination reaction without using a basic aqueous solution such as a sodium hydroxide aqueous solution.

Another object of the present invention is to provide a method for removing HCl in a chlorination reaction with little loss of a final product at a high HCl removal rate.

Technical Solution

In one general aspect, a method for removing HCl in a chlorination reaction includes, in a chlorination reaction in which a final product with a chlorine-substituted terminal is produced in a plurality of column reactors connected to each other in series, heating hydrogen chloride produced in the chlorination reaction in a stripping column connected to the reactor positioned at the rearmost end, to remove hydrogen chloride.

In the method for removing HCl in a chlorination reaction according to an exemplary embodiment of the present invention, the heating of the hydrogen chloride may be performed by high-temperature steam supplied from a reboiler connected to the bottom of the stripping column.

In the method for removing HCl in a chlorination reaction according to an exemplary embodiment of the present invention, a temperature and a pressure at the top in the stripping column may be 10 to 30° C. and 0.5 bar or less, respectively, and a temperature and a pressure at the bottom in the stripping column may be 100 to 150° C. and 1 bar or less, respectively.

In the method for removing HCl in a chlorination reaction according to an exemplary embodiment of the present invention, the high-temperature steam may be supplied in an amount of 5 to 20 parts by weight per unit time with respect to 100 parts by weight of a reaction product supplied from the reactor positioned at the rearmost end.

In the method for removing HCl in a chlorination reaction according to an exemplary embodiment of the present invention, a removal rate of the hydrogen chloride may be 99% or more.

In the method for removing HCl in a chlorination reaction according to an exemplary embodiment of the present invention, a raw material for the chlorination reaction may be an aromatic compound.

In the method for removing HCl in a chlorination reaction according to an exemplary embodiment of the present invention, the chlorination reaction may be performed in each reactor by injecting an equal amount of chlorine gas into the bottom of each reactor, and hydrogen chloride gas generated in each reactor may be partially discharged from each reactor.

In the method for removing HCl in a chlorination reaction according to an exemplary embodiment of the present invention, in the chlorination reaction, a reaction product produced in a front end reactor by a heat exchanger positioned between the reactors may be cooled, and then a predetermined amount of the cooled reaction product may be injected into the bottom of a rear end reactor.

Advantageous Effects

In the method for removing HCl in a chlorination reaction according to the present invention, the hydrogen chloride is removed by heating the hydrogen chloride through the stripping column without using a basic aqueous solution, such that wastewater discharged in the process may be significantly reduced.

In addition, in the method for removing HCl in a chlorination reaction according to the present invention, HCl may be removed at a high removal rate without loss of a final product.

Best Mode

Unless otherwise defined, all the technical terms and scientific terms used in the present specification have the same meanings as commonly understood by those skilled in the art to which the present invention pertains. The description for the known function and configuration unnecessarily obscuring the gist of the present invention will be omitted in the following description and the accompanying drawings.

In addition, unless the context clearly indicates otherwise, the singular forms used in the present specification may be intended to include the plural forms.

In addition, units used in the present specification without special mention are based on weight, and as an example, a unit of % or a ratio means wt % or a weight ratio. Unless otherwise defined, wt % means wt % of any one component in a composition with respect to the total weight of the composition.

In addition, a numerical range used in the present specification includes upper and lower limits and all values within these limits, increments logically derived from a form and span of a defined range, all double limited values, and all possible combinations of the upper and lower limits in the numerical range defined in different forms. Unless otherwise specifically defined in the specification of the present invention, values out of the numerical range that may occur due to experimental errors or rounded values also fall within the defined numerical range.

In the present specification, the expression "comprise(s)" is intended to be an open-ended transitional phrase having an equivalent meaning to "include(s)", "contain(s)", "have (has)", and "is (are) characterized by", and does not exclude elements, materials, or steps, all of which are not further recited herein.

In addition, the term "substantially" used in the present specification means that a specific element, material, or step that is not listed in combination with another element, material, or step may be present in an amount having no unacceptably significant influence on at least one basic and novel technical idea of the present invention.

The present invention includes, in a chlorination reaction in which a final product with a chlorine-substituted terminal is produced in a plurality of column reactors connected to each other in series, heating hydrogen chloride produced in the chlorination reaction in a stripping column connected to the reactor positioned at the rearmost end, to remove hydrogen chloride.

In the related art, in order to remove by-products including a catalyst and hydrogen chloride contained in a reactant, a large amount of basic aqueous solution such as a sodium hydroxide aqueous solution has been added to the reactant, but there is a problem in that a large amount of wastewater is finally generated in an amount that is as much as the basic aqueous solution used.

However, in the present invention, the hydrogen chloride is removed by heating the hydrogen chloride through the stripping column without using a basic aqueous solution, such that wastewater discharged in the process may be significantly reduced. In addition, in the method for removing HCl in a chlorination reaction according to the present invention, HCl may be removed at a high removal rate without loss of a final product.

Specifically, first, in the present invention, in a chlorination reaction in which a final product with a chlorine-substituted terminal is produced in a plurality of column reactors connected to each other in series, HCl produced during the reaction is removed.

In an exemplary embodiment of the present invention, a raw material may be an aromatic compound, and specifically, benzene or toluene. The final product may be a chloride thereof, but is not limited thereto. As a specific example, o-chlorotoluene and p-chlorotoluene may be produced by supplying chlorine gas to toluene, which is an aromatic compound.

More specifically, in the present invention, as the plurality of column reactors are connected to each other in series in the chlorination reaction, a reaction product produced in the frontmost end reactor positioned at the frontmost end and supplied with a raw material and chlorine gas for the first time is supplied to a rear end reactor adjacent thereto, and the reaction product produced in the front end by such a method may be supplied to the reactor positioned at the rearmost end by sequentially passing through the respective reactors arranged in series. In addition, chlorine gas is injected into each reactor, and the raw material and the reaction product that has passed through the front end reactor may undergo a chlorination reaction in each reactor.

In an exemplary embodiment of the present invention, the chlorination reaction is performed in each reactor by injecting an equal amount of chlorine gas into the bottom of each reactor, and hydrogen chloride gas generated in each reactor may be partially discharged from each reactor. In such a chlorination reaction, it is possible to increase a yield of a product produced by preventing a decrease in chlorination reactivity due to generation of foam caused by an increase in gas volume with the lapse of reaction time. In addition, a conversion rate of the product is improved and the production of hydrogen chloride, which is a reaction by-product, is fundamentally reduced, and thus, the method for removing HCl of the present invention may be more advantageous in removing HCl.

In addition, the chlorination reaction of the present invention is an exothermic reaction, and as the reaction proceeds, the temperature of the reaction solution increases. Since selectivity of a chlorination reaction product of an aromatic compound such as o-chlorotoluene or p-chlorotoluene tends to decrease as the reaction temperature increases, a problem in which the selectivity decreases may occur when the reaction proceeds too much. Therefore, the reaction product produced in the front end reactor may be cooled by a heat exchanger positioned between the adjacent reactors, and then a predetermined amount of the cooled reaction product may be injected into the bottom of the rear end reactor.

The cooling may be performed at a temperature of 0° C. or higher and about 50° C. or lower, and specifically, 5° C. or higher and 30° C., but the cooling may be performed without limitation in a range in which chlorine is not liquefied. Specifically, the cooling may be performed at 25° C. when the supply pressure of chlorine gas is 7.81 bara, and may be performed at 10° C. when the supply pressure of chlorine is 5.07 bara. When the supply pressure of chlorine gas is 3.7 bara, the cooling may be performed to 0° C. However, in order to lower the temperature of the chlorine gas, a refrigerant at a temperature lower than the temperature at which cooling is to be performed is required, and cooling more than necessary causes excessive investment costs. Therefore, the above range may be preferable in consideration of chlorine liquefaction temperature, operation cost, and the like according to the operating pressure. However, the cooling is not limited thereto.

The present invention is intended to remove hydrogen chloride produced in the above chlorination reaction, and includes heating hydrogen chloride in a stripping column connected to the rearmost reactor to remove hydrogen chloride. In this case, the stripping column is a multi-stage column, and may be provided with 10 stages to 20 stages, but is not limited thereto.

In this step, the heating of the hydrogen chloride may be performed in a manner that may heat the reaction product supplied from the reactor in the stripping column, specifically, in a manner widely known in the art, such as a heat exchanger or a heater. Preferably, the heating of the hydrogen chloride may be performed by high-temperature steam supplied from a reboiler connected to the bottom of the stripping column. Specifically, the reaction product supplied to the stripping column from the rearmost reactor contains a final product produced through the chlorination reaction and by-products including HCl. As high-temperature steam is supplied to the inside of the stripping column to which the reaction product is supplied to heat HCl, HCl may be distilled and separated from the reaction product. As such, a method for heating and separating HCl by supplying high-temperature steam to the stripping column may extremely lower the solubility of HCl in the reaction product, such that the HCl removal rate may be increased. In addition, the amount of final product to be splashed may be minimized, such that the amount of final product that is lost due to the splash may be minimized. That is, in the present invention, HCl may be removed at a high removal rate with almost no loss of the final product, and therefore, the process efficiency is significantly high.

In an exemplary embodiment of the present invention, a temperature at the top in the stripping column may be 10 to 30° C., and specifically, 15 to 20° C., and a pressure at the top may be bar or less, and specifically, 0.1 bar or less, but the temperature and the pressure are not limited thereto. In this case, a temperature at the bottom in the stripping column to which high-temperature steam is supplied may be 100 to 150° C., and specifically, 120 to 140° C., due to the high-temperature steam, and a pressure at the bottom may be 1 bar or less, and specifically, 0.6 bar or less, but the temperature and the pressure are not limited thereto. However, within these ranges, it is possible to effectively remove HCl while preventing deformation of the final product due to temperature and pressure.

In an exemplary embodiment of the present invention, the high-temperature steam may be supplied without limitation as long as the high-temperature steam is supplied in an amount capable of removing HC from the reaction product supplied from the reactor positioned at the rearmost end, and the high-temperature steam may be preferably supplied in an amount of 5 to 20 parts by weight, and specifically, 8 to 15 parts by weight, per unit time with respect to 100 parts by weight. Within the above range, HCl may be heated and removed by efficiently heating the reaction product without wasting the high-temperature steam.

In the method for removing HCl in a chlorination reaction of the present invention, hydrogen chloride may be removed at a ratio of hydrogen chloride removed to hydrogen chloride produced, that is, a removal rate of hydrogen chloride of 99%, and more specifically, 99.9 or more, which is a high removal rate, such that a high-purity final product may be obtained.

Furthermore, a ratio of the remaining amount of the final product after the HCl removal step to the amount of the final product supplied into the stripping column, that is, a yield of the final product is also 99% or more, such that a high yield of the final product may be maintained.

Hereinafter, preferred Examples and Comparative Examples of the present invention will be described. However, each of the following Examples is merely a preferred example of the present invention, and the present invention is not limited to the following Examples.

EXAMPLE 1

Toluene and chlorine gas were injected into a reactor having an inner diameter of 13 cm and a height of 600 cm, and a linear velocity of gas in the reactor was adjusted by adjusting a linear velocity of chlorine gas to 5 to 10 m/sec and a feed rate of a raw material including toluene to 10 to 40 m/sec. At this time, a molar ratio of toluene to chlorine was 2:1, $FeCl_3$ was used as a catalyst, $S_2Cl_2$ was used as a cocatalyst, and concentrations of $FeCl_3$ and $S_2Cl_2$ were 300 ppm and 150 ppm, respectively.

The reaction product obtained by reaction for 2 hours was injected into a multi-stage stripping column with 14 stages, and then high-temperature steam was supplied to remove HCl. The specific conditions are shown in Table 1.

TABLE 1

| Classification | | Example 1 | Comparative Example 1 | Comparative Example 2 |
|---|---|---|---|---|
| Reactor Product (kg/h) | | 6342.44 | 6313.89 | 6361.26 |
| HCl gas (kg/h) | | 0.015 | 0.01 | 288.99 |
| Product loss amount (kg/h) | | 18.82 | 47.37 | 0.00 |
| HCl gas removal amount (kg/h) | | 288.98 | 288.99 | 0.00 |
| Total number of stages of column | | 14 | 15 | — |
| Temp. (° C.) | Top | 19 | 17 | — |
| | Bottom | 126 | 15 | — |
| Press. (Barg) | Top | 0.1 | 0.1 | — |
| | Bottom | 0.6 | 0.6 | — |
| Amount of high-temperature steam used (kg/h) | | 644.757 | — | — |
| Amount of N2 used (kg/h) | | | 400 | — |

COMPARATIVE EXAMPLE 1

In Example 1, HCl was removed by spraying nitrogen gas without using high-temperature steam. The specific conditions are as shown in Table 1.

COMPARATIVE EXAMPLE 2

In Example 1, only a chlorination reaction was performed without the HCl removal step. The specific conditions are as shown in Table 1.

The specific conditions, the HCl removal amount, and the final product loss amount of Example 1 and Comparative Examples 1 and 2 are shown in Table 1.

Referring to Table 1, in the present invention, it could be confirmed that the removal rate of HCl was 99% or more, and the yield of the final product was 99% or more.

Hereinabove, although the present invention has been described by specific matters, limited exemplary embodiments, and drawings, they have been provided only for assisting in the entire understanding of the present invention. Therefore, the present invention is not limited to the exemplary embodiments. Various modifications and changes may be made by those skilled in the art to which the present invention pertains from this description.

Therefore, the spirit of the present invention should not be limited to the described exemplary embodiments, but the claims and all modifications equal or equivalent to the claims are intended to fall within the spirit of the present invention.

The invention claimed is:

1. A method for removing HCl in a chlorination reaction, the method comprising, in a chlorination reaction in which a final product with a chlorine-substituted terminal is produced in a plurality of column reactors connected to each other in series, heating hydrogen chloride produced in the chlorination reaction in a stripping column connected to the reactor positioned at the rearmost end, to remove hydrogen chloride, wherein only the rearmost reactor among the plurality of column reactors is connected to the stripping column which is a multi-stage column provided with 10 stages to 20 stages, wherein in the chlorination reaction, a liquid-phase reaction product produced in a front end reactor is cooled by a heat exchanger positioned between the reactors to suppress a temperature increase of the reaction product caused by the exothermic chlorination reaction, the cooling being performed within a temperature range in which chlorine gas is not liquefied, and then a predetermined amount of the cooled reaction product is injected into the bottom of a rear end reactor.

2. The method of claim 1, wherein the heating of the hydrogen chloride is performed by a steam supplied from a reboiler connected to the bottom of the stripping column.

3. The method of claim 2, wherein a temperature and a pressure at the top in the stripping column are 10 to 30° C. and 0.5 bar or less, respectively, and a temperature and a pressure at the bottom in the stripping column are 100 to 150° C. and 1 bar or less, respectively.

4. The method of claim 2, wherein the steam is supplied in an amount of 5 to 20 parts by weight per unit time with respect to 100 parts by weight of a reaction product supplied from the reactor positioned at the rearmost end.

5. The method of claim 2, wherein a removal rate of the hydrogen chloride is 99% or more.

6. The method of claim 1, wherein a raw material for the chlorination reaction is an aromatic compound.

7. The method of claim 1, wherein the chlorination reaction is performed in each reactor by injecting an equal amount of chlorine gas into the bottom of each reactor, and hydrogen chloride gas generated in each reactor is partially discharged from each reactor.

8. The method of claim 1, wherein the cooling is performed at a temperature of between 0° C. and about 50° C.

* * * * *